United States Patent [19]

Yamamoto et al.

[11] 4,096,144
[45] Jun. 20, 1978

[54] PROCESS FOR PREPARING QUINAZOLINONE DERIVATIVES AND THEIR 2-(N-MONO-SUBSTITUTED AMINO)-PHENYL KETONE INTERMEDIATE DERIVATIVES

[75] Inventors: Michihiro Yamamoto, Toyonaka; Masao Koshiba; Shigeho Inaba, both of Takarazuka; Hisao Yamamoto, Nishinomiya, all of Japan

[73] Assignee: Sumitomo Chemical Company, Limited, Osaka, Japan

[21] Appl. No.: 592,241

[22] Filed: Jul. 1, 1975

Related U.S. Application Data

[63] Continuation of Ser. No. 203,049, Nov. 29, 1971, abandoned.

[30] Foreign Application Priority Data

Dec. 8, 1970  Japan .................................. 45-109975

[51] Int. Cl.$^2$ ..................... C07D 239/82; C07C 97/10
[52] U.S. Cl. .............................. 544/284; 260/326.5 J; 260/332.3 R; 260/347.7; 260/570 R; 260/570 AB; 544/119; 544/286

[58] Field of Search ................. 260/256.4 Q, 251 QB, 260/570 R, 570 AB, 326.5 J, 332.3 R, 347.7

[56] References Cited

U.S. PATENT DOCUMENTS

| | | | |
|---|---|---|---|
| 2,809,994 | 10/1957 | Hinckley | 260/577 |
| 3,109,843 | 11/1963 | Reeder et al. | 260/570 |

OTHER PUBLICATIONS

Ott et al., "Chemical Abstracts," vol. 71, p. 302, 30502y (1969).

Primary Examiner—Paul M. Coughlan, Jr.
Attorney, Agent, or Firm—Stevens, Davis, Miller & Mosher

[57] ABSTRACT

1,4-Substituted-2(1H)-quinazolinone derivatives are prepared by contactng a 2-aminophenyl ketone derivative with an alkaline agent such as alkali metal, alkali metal hydride, alkali metal amide, etc., reacting the thus obtained metal salt of 2-aminophenyl ketone derivative with a reactive ester of alcohols, reacting the thus obtained 2-(N-mono-substituted amino)-phenyl ketone derivative with a lower alkyl haloformate or a benzyl haloformate, and reacting the thus obtained carbamate derivative with ammonia. The 1,4-substituted-2(1H)-quinazolinone derivatives have excellent pharmacological properties, particularly as anti-inflammatory and analgesic effects.

9 Claims, No Drawings

PROCESS FOR PREPARING QUINAZOLINONE DERIVATIVES AND THEIR 2-(N-MONO-SUBSTITUTED AMINO)-PHENYL KETONE

This is a continuation of application Ser. No. 203,049 filed Nov. 29, 1971, now abandoned.

This invention relates to a novel process for producing quinazoline derivatives.

More particularly, this invention pertains to a novel process for preparing quinazolinone derivatives represented by the formula,

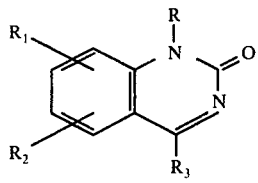

wherein $R_1$ and $R_2$ are individually a hydrogen atom, a lower alkyl group, a lower alkoxy group, a nitro group, a trifluoromethyl group, a lower alkylthio group, a lower alkylsulfonyl group or a halogen atom; $R_3$ is a phenyl group, a halophenyl group, a lower alkylphenyl group, a lower alkoxyphenyl group, a trifluoromethylphenyl group, a lower cycloalkyl group, a lower cycloalkenyl group, a pyridyl group, a furyl group, a thienyl group or a naphthyl group; and R is a lower alkyl group, a lower alkenyl group, a lower haloalkyl group, an aralkyl group, a lower cycloalkyl group, a lower cycloalkylalkyl group, a lower aldoxyalkyl group, a lower hydroxyalkyl group, a lower alkanoyloxyalkyl group, a lower trihalomethylalkyl group, a lower alkylthioalkyl group or a group of the formula

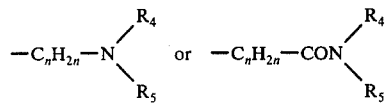

(wherein n is an integer of 1 to 3; $R_4$ and $R_5$ are individually an alkyl group, provided that $R_4$ and $R_5$ may form together with the adjacent nitrogen atom an unsubstituted or optionally substituted 5- or 6-membered heterocyclic ring, which may further contain a hetero atom.)

In the compounds represented by the general formula (I), the term "alkyl" means both straight and branched chain aliphatic hydrocarbon radicals, and the lower alkyl group includes for example, methyl, ethyl, n-propyl, isopropyl, n-butyl, isobutyl and tertiary-butyl groups; the lower alkoxy group includes, for example, methoxy, ethoxy, n-propoxy, isopropoxy, n-butoxy and tertiary- butoxy groups; the lower alkylthio group includes, for example, methylthio, ethylthio and butylthio groups; the term "halogen" comprehends all halogens (e.g. fluorine, chlorine, bromine and iodine); the lower cycloalkyl group includes, for example, cyclopropyl, cyclobutyl, cyclopentyl and cyclohexyl groups; the lower cycloalkenyl group includes, for example, cyclopentenyl and cyclohexenyl groups; the the lower alkenyl group includes, for example, vinyl, allyl, methallyl, butenyl and crotyl groups; the aralkyl group includes, for example, benzyl, phenethyl, chlorobenzyl and fluorobenzyl groups; the lower alkanoyloxy group includes, for example, acetoxy and propionyloxy groups; and the trihalomethyl group includes, for example, trifluoromethyl, trichloromethyl and chlorodifluoromethyl groups. The alkylene group represented by $C_nH_{2n}$ is a straight chain or branched chain alkylene group having 1 to 3 carbon atoms, and includes, for example, methylene, ethylene, 1-methylethylene, 2-methylethylene and trimethylene groups. $R_4$ and $R_5$ may form together with the adjacent nitrogen atom a heterocyclic ring, and the heterocyclic group includes, for example, pyrrolidino, piperidino and morpholino groups and substituted derivatives thereof.

The quinazoline derivatives of the formula (I), which include novel compounds, and have excellent pharmacological properties, particularly as anti-inflammatory and analgesic effects and they are also useful as intermediates for the synthesis of other medicines. The anti-inflammatory activity of these compounds is more potent than that of 1,2-diphenyl-3,5-dioxo-4-n-butylpyrazolidine (phenylbutazone), and the acute, subacute and chronic toxicities are much lower than those of phenylbutazone.

Thus the present invention offers a novel and useful process for producing commercially such valuable compounds.

A few processes for producing some of these quinazoline derivatives have heretofore been described. For instance, it is known to obtain a quinazoline derivative by fusing a 2-aminophenyl ketone derivative with urea, and further, alkylating the resulting compound (Netherland Pat. No. 67-16429) or by reacting a 2-aminophenyl ketone derivative with an arylsulfonic acid or a derivative thereof, alkylating the 2-arylsulfonylaminophenyl ketone derivative thus obtained to yield a 2-alkylaminophenyl ketone arylsulfonate, then splitting the arylsulfonyl group to obtain a 2-alkylaminophenyl ketone derivative (J. Org. Chem., 27, 3781 (1962)), and further fusing the compound with an alkyl carbamate (Netherland Pat. No. 68-00104). However, these prior processes are not very applicable to large scale manufacture.

Contrary to these procedures, the present inventors have found that quinazoline derivatives of the formula (I) may be smoothly and economically prepared in high yield and high purity by contacting a 2-aminophenyl ketone derivative represented by the formula,

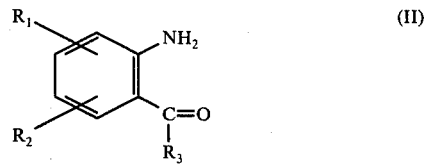

wherein $R_1$, $R_2$ and $R_3$ are as defined above, with an alkaline agent such as an alkali metal, alkali metal hydride, alkali metal amide or organolithium compound to form a metal salt of 2-aminophenyl ketone derivative represented by the formula,

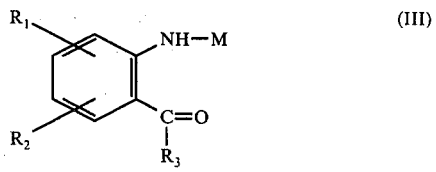

wherein $R_1$, $R_2$ and $R_3$ are as defined above; and M is an alkali metal atom, and reacting the resultant metal salt with a reactive ester of a compound represented by the formula, $$R - OH \quad (IV)$$

wherein R is as defined above, to prepare a 2-(N-monosubstituted amino)phenyl ketone derivative represented by the formula,

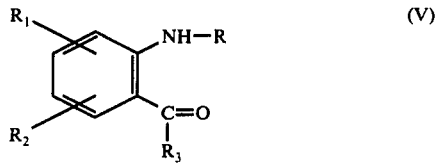

(V)

wherein $R_1$, $R_2$, $R_3$ and R are as defined above, and then reacting the compound of the formula (V) with a lower alkyl haloformate or a benzyl haloformate to yield a carbamate derivative represented by the formula,

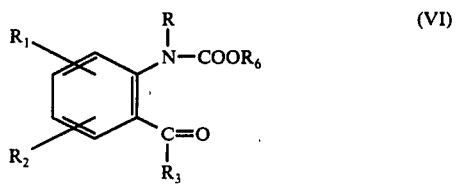

(VI)

wherein $R_1$, $R_2$, $R_3$ and R are as defined above; and $R_6$ is a lower alkyl group or a benzyl group, and finally reacting the carbomate derivative of the formula (VI) with ammonia.

Such process for producing quinazoline derivatives has not heretofore been described in any literature, and thus it differs markedly from the known methods and represents an improvement thereover. The process of the present invention will be explained in detail below.

In the first place, the 2-(N-mono-substituted amino)-phenyl ketone derivatives of the formula (V), which include novel compounds, may be easily prepared by contacting the 2-aminophenyl ketone derivatives of the formula (II) with an alkaline agent such as alkali metal, alkali metal hydride, alkali metal amide or organolithium compound in the presence of a solvent, and then, with or without isolation of the metal salt of the formula (III) thus obtained, reacting it with a reactive ester of the compound of the formula (IV) in the presence of a solvent.

Examples of the alkali metal include lithium, sodium and potassium. Examples of the alkali metal hydride include sodium hydride and potassium hydride. Examples of the alkali metal amide include sodium amide and potassium amide. And examples of organolithium compound include butyl lithium and phenyl lithium.

The suitable reactive esters are hydrohalic acid esters such as the chlorides, bromides and iodides, and sulfonic acid esters such as trichloromethanesulfonate, benzenesulfonate and p-toluenesulfonate.

The suitable solvents employed in these processes include benzene, toluene, xylene, monochlorobenzene, dimethylacetamide, diethylacetamide, dimethylformamide, dioxane, dimethylsulfoxide and a mixture thereof.

In these processes, there is preferably used, one equivalent or some excess amount of each of the alkaline agents and the reactive ester of the compound of the formula (IV) per mole of the starting compound of the formula (II). The formation of the metal salt of the formula (III) is carried out under cooling or heating, according to the solvent employed, and the following substitution reaction is generally effected at a temperature ranging from room temperature to the boiling point of the solvent employed.

In the next place, the above obtained 2-(N-mono-substituted amino)phenyl ketone derivatives of the formula (V) may be converted to the desired quinazoline derivatives of the formula (I) via carbamate derivatives of the formula (VI).

The carbamate derivatives of the formula (VI), which include novel compounds, may be easily prepared by reacting the 2-(N-mono-substituted amino)-phenyl ketone derivatives with a lower alkyl haloformate (e.g. methyl chloroformate, ethyl chloroformate, isopropyl chloroformate or the like) or a benzyl haloformate in the presence or absence of a solvent and a basic condensing agent.

The suitable solvent is selected from the group consisting of ether, isopropyl ether, tetrahydrofuran, benzene, toluene, xylene, chlorobenzene, chloroform, dichloroethane and the like. An excess of the haloformate may be used without a solvent.

The condensing agent includes, for example, an inorganic base such as sodium hydroxide, potassium hydroxide, sodium carbonate or potassium carbonate or an organic base such as pyridine, triethylamine or dimethylaniline.

Further, according to the present invention the quinazoline derivatives can be obtained by heating the carbamate derivatives of the formula (VI) with ammonia.

The reaction may be advantageously carried out in the presence of a solvent or solvent mixture. Examples of the solvent include methanol, ethanol, isopropanol, tertiary-butanol, Cellosolve, ethylene glycol, diethylene glycol, dioxane, acetone, pyridine, benzene, toluene, xylene, dimethylsulfoxide and dimethylformamide and a mixture thereof. Ammonia is added to the reaction mixture as gaseous ammonia, alcoholic ammonia (e.g. methanolic or ethanolic ammonia), liquid ammonia or ammonium salt (e.g. ammonium acetate, ammonium formate, ammonium carbamate, ammonium phosphate or ammonium carbonate) which is generating ammonia during the reaction. When the ammonium salt is used, the reaction may be effected in the presence or absence of a base such as, sodium hydroxide, potassium hydroxide, potassium carbonate, sodium methylate, sodium ethylate, potassium ethylate, triethylamine or pyridine.

The reaction may alternatively be carried out by heating the aforesaid compound in liquid ammonia or fusing the compound together with an ammonium salt. After completion of the reaction, the reaction mixture is concentrated, or diluted with water, and the resulting precipitate is washed with such a solvent as ether or alcohol, to obtain the desired quinazoline derivative.

According to the process of the present invention, there are obtained, for example, the following 2-(N-mono-substituted amino)phenyl ketone derivatives and quinazoline derivatives.

2-Methylamino-5-chlorobenzophenone, m.p. 95° – 96° C.

2-Methylamino-5-iodobenzophenone, m.p. 107° – 108° C.

2-Methylamino-5,2'-dichlorobenzophenone, m.p. 88° - 90° C.
2-Methylamino-5-nitrobenzophenone, m.p. 167° - 168° C.
2-Methylamino-5-methylthiobenzophenone, m.p. 66° - 67° C.
2-Methylamino-5-methylsulfonylbenzophenone, m.p. 173° - 174° C.
2Methylaminophenyl 2-thienyl ketone, yellow oil
2-Ethylamino-5-methylbenzophenone, m.p. 54° - 55° C.
2-Ethylamino-5-nitrobenzophenone, m.p. 132° - 133° C.
2-Ethylamino-5-trifluoromethylbenzophenone, m.p. 78° - 80° C.
2-Isopropylaminobenzophenone, yellow oil.
2-Isopropylamino-5-chlorobenzophenone, m.p. 74.5° - 75.5° C.
2-Isopropylamino-5-nitrobenzophenone, m.p. 155° - 156° C.
2-Isopropylamino-4,5-dimethylbenzophenone, yellow oil.
2-Isobutylamino-5-chlorobenzophenone, m.p. 54° - 56° C.
2-Allylamino-5-chlorobenzophenone, m.p. 77° - 78° C.
2-Benzylamino-5-chlorobenzophenone, m.p. 86° - 87° C.
2-Benzylamino-5-nitrobenzophenone, m.p. 118° - 119° C.
2-Cyclopropylmethylamino-5-chlorobenzophenone, m.p. 84° - 85° C.
2-Cyclopropylmethylamino-4-chlorobenzophenone, yellow oil.
2-Cyclopropylmethylamino-3-chlorobenzophenone, yellow oil.
2-Cyclopropylmethylamino-3,5-dichlorobenzophenone, m.p. 96.5° - 97.5° C.
2-Cyclopropylmethylamino-5-fluorobenzophenone, m.p. 97.5° - 98.5° C.
2-Cyclopropylmethylamino-5-methoxybenzophenone, yellow oil.
2-Cyclopropylmethylamino-5-trifluoromethylbenzophenone, m.p. 107° - 108° C.
2-Cyclohexylethylamino-5-chlorobenzophenone, m.p. 63° - 64° C.
2-Cyclopropylmethylamino-5-chlorophenyl 2-thienyl ketone, yellow oil.
2-Cyclopropylmethylamino-5-chlorophenyl cyclohexyl ketone, yellow oil.
2-Cyclopropylmethylamino-5-chlorophenyl 2-pyridyl ketone, m.p. 87° - 88° C.
2-Cyclohexylamino-5-chlorobenzophenone, yellow oil.
2-(2'-Ethoxyethylamino)-5-chloro-2'-fluorobenzophenone, yellow oil.
2-(2',2',2'-Trifluoroethylamino)-5-chlorobenzophenone, m.p. 99° - 100° C.
2-(2'-Hydroxyethylamino)-5-nitrobenzophenone, m.p. 120.5° - 121.5° C.
2-(2'-Diethylaminoethylamino)-5-chloro-2'-fluorobenzophenone, yellow oil.
2-(2'-morpholino ethyl amino)-5-nitrobenzophenone, yellow oil.
1-Methyl-4-phenyl-6-chloro-2(1H)-quinazolinone, m.p. 220° - 221° C.
1-Methyl-4-phenyl-6-iodo-2(1H)-quinazolinone, m.p. 247° - 248° C.
1-Methyl-4-phenyl-6-trifluoromethyl-2(1H)-quinazolinone, m.p. 198° - 200° C.
1-Methyl-4-(o-chlorophenyl)-6-chloro-2(1H)-quinazolinone, m.p. 198° C.
1-Methyl-4-(m-chlorophenyl)-6-methoxy-2(1H)-quinazolinone, m.p. 197° - 198° C.
1-Methyl-4-(p-methoxyphenyl)-6-chloro-2(1H)-quinazolinone, m.p. 214° - 215° C.
1-Methyl-4-phenyl-6-methylthio-2(1H)-quinazolinone, m.p. 156° - 157° C.
1-Methyl-4-phenyl-6-methylsulfonyl-2(1H)-quinazolinone, m.p. 238° C.
1-Methyl-4-phenyl-6-nitro-2(1H)-quinazolinone, m.p. 263° - 264° C.
1-Methyl-4-(2'-thienyl)-2(1-H)-quinazolinone, m.p. 149° - 150° C.
1-Ethyl-4-(o-tolyl)-6-chloro-2(1H)-quinazolinone, m.p. 174° - 175° C.
1-Ethyl-4-phenyl-6-methyl-2(1H)-quinazolinone, m.p. 180° C.
1-Ethyl-4-phenyl-6,7-dimethyl-2(1H)-quinazolinone, m.p. 176° - 178° C.
1-Ethyl-4-phenyl-6,7-dimethoxy-2(1H)-quinazolinone, m.p. 175° C.
1-Ethyl-4-phenyl-6-methylthio-2(1H)-quinazolinone, m.p. 150° - 151° C.
1-Ethyl-4-phenyl-6-nitro-2(1H)-quinazolinone, m.p. 214° - 215° C.
1-Ethyl-4-phenyl-6-trifluoromethyl-2(1H)-quinazolinone, m.p. 180° C.
1-Ethyl-4-(2'-thienyl)-2(1H)-quinazolinone, m.p. 157° - 158° C.
1-Isopropyl-4-phenyl-2(1H)-quinazolinone, m.p. 140° C.
1-Isopropyl-4-phenyl-6-chloro-2(1H)-quinazolinone, m.p. 149° - 150° C.
1-Isopropyl-4-phenyl-7-methyl-2(1H)-quinazolinone, m.p. 135° - 137° C.
1-Isopropyl-4-phenyl-6,7-dimethyl-2(1H)-quinazolinone, m.p. 135° - 136° C.
1-Isopropyl-4-phenyl-6-nitro-2(1H)-quinazolinone, m.p. 190° - 192° C.
1-Isopropyl-4-phenyl-7-methoxy-2(1H)-quinazolinone, m.p. 133° - 135° C.
1-Allyl-4-phenyl-6-nitro-2(1H)-quinazolinone, m.p. 201° - 202° C.
1-Allyl-4-phenyl-6-chloro-2(1H)-quinazolinone, m.p. 182° - 183° C.
1-(3',3'-Dimethylallyl)-4-phenyl-6-chloro-2(1H)-quinazolinone, m.p. 134° - 136° C.
1Allyl-4-(2'-thienyl)-2(1H)-quinazolinone, m.p. 116° - 118° C.
1-(3'-Chloropropyl)-4-phenyl-6-chloro-2(1H)-quinazolinone, m.p. 145° - 146° C.
1-Benzyl-4-phenyl-6-nitro-2(1H)-quinazolinone, m.p. 173° - 174° C.
1-Benzyl-4-phenyl-6-chloro-2(1H)-quinazolinone, m.p. 182° C.
1-(o-Fluorobenzyl)-4-phenyl-6-chloro-2(1H)-quinazolinone, m.p. 145° - 146° C.
1-Cyclopropylmethyl-4-phenyl-2(1H)-quinazolinone, m.p. 154° - 155° C.
1-Cyclopropylmethyl-4-phenyl-6-fluoro-2(1H)-quinazolinone, m.p. 168° - 169° C.
1-Cyclopropylmethyl-4-phenyl-6-bromo-2-(1H)-quinazolinone, m.p. 163° - 164° C.
1-Cyclopropylmethyl-4-phenyl-7-chloro-2(1H)-quinazolinone, m.p. 169° - 170° C.

1-Cyclopropylmethyl-4-phenyl-8-chloro-2(1H)-quinazolinone, m.p. 163° – 164° C.

1-Cyclopropylmethyl-4-phenyl-6,7-dichloro-2(1H)-quinazolinone, m.p. 206° – 207° C.

1-Cyclopropylmethyl-4-phenyl-6,8-dichloro-2(1H)-quinazolinone, m.p. 158° – 159° C.

1-Cyclopropylmethyl-4-phenyl-6-methyl-2(1H)-quinazolinone, m.p. 162° – 163° C.

1-Cyclopropylmethyl-4-phenyl-6-chloro-2(1H)-quinazolinone, m.p. 172° – 173° C.

1-Cyclopropylmethyl-4-phenyl-6-methoxy-2(1H)-quinazolinone, m.p. 115° – 116° C.

1-Cyclopropylmethyl-4-phenyl-6-nitro-2(1H)-quinazolinone, m.p. 172° – 173° C.

1-Cyclopropylmethyl-4-phenyl-6-methylsulfonyl-2(1H)-quinazolinone, m.p. 186° – 187° C.

1-Cyclopropylmethyl-4-phenyl-6-trifluoromethyl-2(1H)-quinazolinone, m.p. 166° – 167° C.

1-Cyclopropylmethyl-4-(o-fluorophenyl)-6-chloro-2(1H)-quinazolinone, m.p. 168° – 169° C.

1-Cyclopropylmethyl-4-(p-tolyl)-2(1H)-quinazolinone, m.p. 159° – 160° C.

1-Cyclopropylmethyl-4-(p-methoxyphenyl)-6-chloro-2(1H)-quinazolinone, m.p. 169.5° – 170° C.

1-Cyclopropylmethyl-4-(2'-pyridyl)-6-chloro-2(1H)-quinazolinone, m.p. 120° – 121° C.

1-Cyclopropylmethyl-4-cyclohexyl-6-chloro-2(1H)-quinazolinone, m.p. 156° – 157° C.

1-Cyclopropylmethyl-4-(2'-thienyl)-6-chloro-2(1H)-quinazolinone, m.p. 134.5° – 135.5° C.

1-Cyclobutylmethyl-4-phenyl-6-chloro-2(1H)-quinazolinone, m.p. 115° – 116° C.

1-Cyclopentylmethyl-4-phenyl-6-chloro-2(1H)-quinazolinone, m.p. 222° – 223° C.

1-Cyclohexylmethyl-4-phenyl-6-chloro-2(1H)-quinazolinone, m.p. 224° – 225° C.

1-Cyclohexylethyl-4-phenyl-6-chloro-2(1H)-quinazolinone, m.p. 115° – 116° C.

1-Cyclohexyl-4-phenyl-6-chloro-2(1H)-quinazolinone, m.p. 120° C.

1-Methoxymethyl-4-phenyl-6-chloro-2(1H)-quinazolinone, m.p. 165° – 166° C.

1-(2'-Ethoxyethyl)-4-(o-fluorophenyl)-6-chloro-2(1H)-quinazolinone, m.p. 146° – 147° C.

1-(2'-Ethoxyethyl)-4-phenyl-6-nitro-2(1H)-quinazolinone, m.p. 128° – 129° C.

1-(2'-Hydroxyethyl)-4-(o-fluorophenyl)-6-chloro-2(1H)-quinazolinone, m.p. 196° – 197° C.

1-(2'-Hydroxyethyl)-4-phenyl-6-nitro-2(1H)-quinazolinone, m.p. 224° – 225° C.

1-(2'-Methylthioethyl)-4-phenyl-6-nitro-2(1H)-quinazolinone, m.p. 140.5° – 141.5° C.

1-(2',2',2'-Trifluoroethyl)-4-phenyl-6-chloro-2(1H)-quinazolinone, m.p. 185° – 186° C.

1-(2'-Diethylaminoethyl)-4-phenyl-6-nitro-2(1H)-quinazolinone (hydrochloride), m.p. 251.5° – 252.5° C (dec.).

1-(2'-Diethylaminoethyl)-4-(o-fluorophenyl)-6-chloro-2(1H)-quinazolinone (hydrochloride), m.p. 222° – 223° C (dec.).

1-(2-morpholino ethyl)-4-phenyl-6-nitro-2-(1H)-quinazolinone, m.p. 78° C.

This invention is further disclosed in the following Example of more preferred embodiments thereof, which are presented for the purpose of illustration and it is not intended to limit the scope of the invention.

Example

To a solution of 6.95 g of 2-amino-5-chlorobenzophenone was added portionwise 1.37 g of 63 % sodium hydride. After the mixture was stirred at room temperature for 30 minutes, 5.62 g of ethyl iodide was added dropwise thereto, and the reaction mixture was further stirred at room temperature for 2 hours. Then, the mixture was poured into 400 ml of water and extracted twice with 100 ml of methylene chloride. The extracts were combined, washed with diluted hydrochloric acid, followed by water and dried over anhydrous sodium sulfate. The solvent was removed under reduced pressure, and the residue was chromatographed on silica gel using chloroform as an eluent to give 7.1 g of 2-ethylamino-5-chlorobenzophenone as red oil, which was recrystalized from ethanol-cyclohexane to give yellow prisms having a melting point of 57° – 58° C.

Subsequently, a mixture of 5.2 g of 2-ethylamino-5-chlorobenzophenone thus obtained and 20 ml of ethyl chloroformate was heated at 110° C for 5 hours. Then, the reaction mixture was concentrated to dryness under reduced pressure to give 2-(N-ethyl-ethoxycarbonylamino)-5-chlorobenzophenone as brown oil.

The compound thus obtained was dissolved in 100 ml of dimethylsulfoxide. To the solution was added 16 g of ammonium acetate and 2.4 g of potassium hydroxide, and the mixture was heated with stirring in an oil bath at 130° C (bath temperature) for 20 hours. After cooling, the reaction mixture was poured into 500 ml of water, the precipitate was collected by filtration, washed successively with ether and water, and dried to give 1-ethyl-4-phenyl-6-chloro-2(1H)-quinazolinone as pale yellow crystals, which was recrystalized from ethanol to give pale yellow needles, having a melting point of 176.5° – 177.5° C.

What is claimed is:

1. A process for producing quinazoline derivatives represented by the formula, $$\text{(I)}$$

wherein $R_1$ and $R_2$ are individually a hydrogen atom, a $C_1$–$C_4$ alkyl group, a $C_1$–$C_4$ alkoxy group, a nitro group, a trifluoromethyl group, a $C_1$–$C_4$ alkylthio group, a $C_1$–$C_4$ alkylsulfonyl group or a halogen atom; $R_3$ is a phenyl group, a halophenyl group, a $C_1$–$C_4$ alkylphenyl group, a $C_1$–$C_4$ alkoxyphenyl group, a trifluoromethylphenyl group, a $C_3$–$C_6$ cycloalkyl group, a $C_5$–$C_6$ cycloalkenyl group, a pyridyl group, a furyl group, a thienyl group or a naphthyl group; and R is a $C_1$–$C_4$ alkyl group, a $C_2$–$C_4$ alkenyl group, a $C_1$–$C_4$ haloalkyl group, a benzyl, phenethyl, chlorobenzyl or fluorobenzyl group, a $C_3$–$C_6$ cycloalkyl group, a $C_3$–$C_6$ cycloalkyl $C_1$–$C_4$ alkyl group, a $C_1$–$C_4$ alkoxy $C_1$–$C_4$ alkyl group, a $C_1$–$C_4$ hydroxyalkyl group, a $C_1$–$C_4$ alkanoyloxy $C_1$–$C_4$ alkyl group, a trihalomethyl $C_1$–$C_4$ alkyl group, a $C_1$–$C_4$ alkylthioalkyl group or a group of the formula

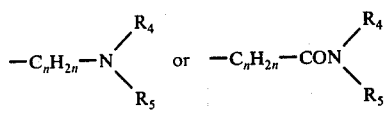

(wherein n is an integer of 1 to 3; $R_4$ and $R_5$ are individually a $C_1$-$C_4$ alkyl group provided that $R_4$ and $R_5$ may form together with the adjacent nitrogen atom an unsubstituted or optionally substituted 5-or 6-membered heterocyclic ring, which may further contain a hetero atom), which comprises contacting a 2-aminophenyl ketone derivative represented by the formula,

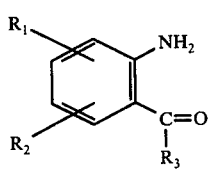

(II)

wherein $R_1$, $R_2$ and $R_3$ are as defined above, with an alkali metal hydride to form a metal salt of 2-aminophenyl ketone derivative represented by the formula,

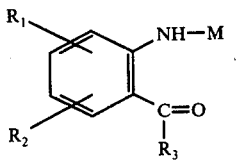

(III)

wherein $R_1$, $R_2$ and $R_3$ are as defined above; and M is an alkali metal atom, thereafter reacting the resultant metal salt of the formula (III) with a compound of the formula RX where R is as defined above and X is halogen to prepare a 2-(N-mono-substituted amino) phenyl ketone derivative represented by the formula,

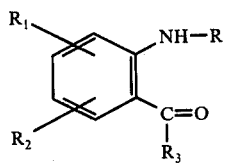

(V)

wherein $R_1$, $R_2$, $R_3$ and R are as defined above, and then, reacting the compound of the formula (V) with a lower alkyl haloformate or a benzyl haloformate to yield a carbamate derivative represented by the formula,

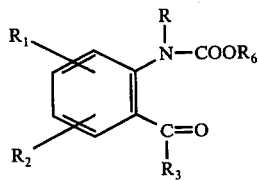

(VI)

wherein $R_1$, $R_2$, $R_3$ and R are as defined above; and $R_6$ is a $C_1$-$C_4$ alkyl group or a benzyl group, and finally reacting the compound of the formula (VI) with ammonia.

2. A process for producing 2-(N-mono-substituted amino)-phenyl ketone derivatives represented by the formula,

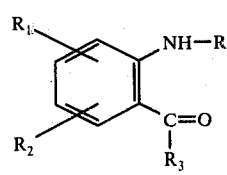

(V)

wherein $R_1$, $R_2$, $R_3$ and R are as defined in claim 1, which comprises contacting a 2-aminophenyl ketone derivative represented by the formula,

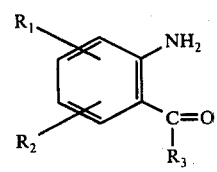

(II)

wherein $R_1$, $R_2$ and $R_3$ are as defined in claim 1, with an alkali metal hydride to form a metal salt of 2-aminophenyl ketone derivative represented by the formula,

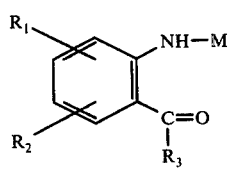

(III)

wherein $R_1$, $R_2$, $R_3$ and M are as defined in claim 1, and reacting the resultant metal salt of the formula (III) with a compound of the formula RX where R is as defined above and X is halogen.

3. A process according to claim 2, wherein the compound of the formula (V), is prepared by reacting the metal salt (III) with the compound of the formula RX in a solvent.

4. A process according to claim 2, wherein the alkali metal hydride is sodium hydride or potassium hydride.

5. A process according to claim 3, wherein the solvent is selected from the group consisting of benzene, toluene, xylene, monochlorobenzene, dimethylacetamide, diethylacetamide, dimethylformamide, dioxane, dimethylsulfoxide and a mixture thereof.

6. A process for producing 2-(N-mono-substituted)-phenyl ketone derivatives represented by the formula,

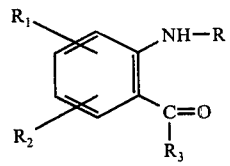

(V)

wherein $R_1$ and $R_2$ are individually a hydrogen atom, a $C_1$-$C_4$ alkyl group, a $C_1$-$C_4$ alkoxy group, a nitro group, a trifluoromethyl group, a $C_1$-$C_4$ alkylthio group, a $C_1$-$C_4$ alkylsulfonyl group or a halogen atom; $R_3$ is a phenyl group, a halophenyl group, a $C_1$-$C_4$ alkylphenyl group, a $C_1$-$C_4$ alkoxyphenyl group, a trifluoromethylphenyl group, a $C_3$-$C_6$ cycloalkyl group, a $C_5$-$C_6$ cycloalkenyl group, or a naphthyl group; and R is a $C_1$-$C_4$ alkyl group, a $C_2$-$C_4$ alkenyl group, a benzyl, phenethyl, chlorobenzyl or fluorobenzyl group, a $C_3$-$C_6$ cycloalkyl group, a $C_3$-$C_6$ cycloalkyl $C_1$-$C_4$ alkyl group, or a trihalomethyl $C_1$-$C_4$ alkyl group which comprises contacting a 2-aminophenyl ketone derivative represented by the formula,

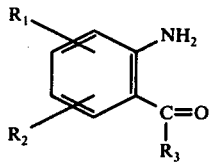
(II)

wherein $R_1$, $R_2$ and $R_3$ are as defined above, with one equivalent or some excess amount of sodium hydride in dimethylformamide to form a sodium salt of 2-aminophenyl ketone derivative represented by the formula,

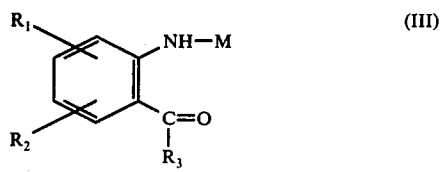
(III)

wherein $R_1$, $R_2$ and $R_3$ are as defined above; and M is a sodium atom, thereafter reacting the resultant metal salt of the formula (III) with one equivalent or some excess amount of a compound of the formula RX where R is as defined above and X is halogen in dimethylformamide at room temperature.

7. A process according to claim 6 for producing 2-ethylamino-5-chlorobenzylphenone, wherein the compound of the formula RX is ethyl iodide, $R_1$ is hydrogen, $R_2$ is chlorine and $R_3$ is a phenyl group.

8. A process according to claim 1, wherein X is chlorine, bromine or iodine.

9. A process according to claim 6, wherein X is chlorine, bromine or iodine.

* * * * *